(12) United States Patent
Jones

(10) Patent No.: US 7,343,917 B2
(45) Date of Patent: Mar. 18, 2008

(54) CLEAR CYCLE FOR VENTILATION DEVICE

(75) Inventor: Richard Llewelyn Jones, Hornsby Heights (AU)

(73) Assignee: ResMed Limited, Bella Vista (AU)

( * ) Notice: Subject to any disclaimer, the term of this patent is extended or adjusted under 35 U.S.C. 154(b) by 709 days.

(21) Appl. No.: 10/944,869

(22) Filed: Sep. 21, 2004

(65) Prior Publication Data

US 2005/0061321 A1    Mar. 24, 2005

Related U.S. Application Data

(60) Provisional application No. 60/503,897, filed on Sep. 22, 2003.

(51) Int. Cl.
*A61M 16/00* (2006.01)

(52) U.S. Cl. ............................. 128/204.21

(58) Field of Classification Search ........ 128/204.18, 128/204.21–204.29, 205.12, 205.23, 205.27
See application file for complete search history.

(56) References Cited

U.S. PATENT DOCUMENTS

| | | |
|---|---|---|
| 4,765,325 A | 8/1988 | Crutchfield |
| 4,846,166 A | 7/1989 | Willeke |
| 5,065,756 A | 11/1991 | Rapoport |
| 5,107,831 A | 4/1992 | Halpern et al. |
| 5,148,802 A | 9/1992 | Sanders et al. |
| 5,289,819 A | 3/1994 | Kroger et al. |
| 5,313,937 A | 5/1994 | Zdrojkowski |
| 5,458,137 A | 10/1995 | Axe et al. |
| 5,529,056 A | 6/1996 | Brunson et al. |
| 5,535,738 A | 7/1996 | Estes et al. |
| 5,535,739 A | 7/1996 | Rapoport et al. |
| 5,540,219 A | 7/1996 | Mechlenberg et al. |
| 5,546,789 A | 8/1996 | Balke et al. |
| 5,558,086 A | 9/1996 | Smith et al. |
| 5,603,316 A | 2/1997 | Coufal et al. |
| 5,617,849 A | 4/1997 | Springett et al. |
| 5,632,269 A | 5/1997 | Zdrojkowski |

(Continued)

FOREIGN PATENT DOCUMENTS

EP    483 566    5/1992

(Continued)

OTHER PUBLICATIONS

U.S. Appl. No. 10/035,199, filed Jan. 2002, Brewer et al.

*Primary Examiner*—Steven O. Douglas
(74) *Attorney, Agent, or Firm*—Nixon & Vanderhye P.C.

(57) ABSTRACT

A method and apparatus are used to perform a clear cycle. The apparatus includes a flow generator in fluid communication with a patient interface via a conduit arranged in a flow path, and sensors to monitor pressures in the flow path. The method includes examining a plurality of operational parameters, determining whether the flow generator should generate flow based on at least one of the plurality of operational parameters, warning the patient to avoid interfacing with the patient interface of the ventilation device prior to generating the flow, and operating the flow generator to generate the flow in accordance with at least one of the plurality of operational parameters. The clear cycle can dislodge debris or water condensate from the flow path. The clear cycle can incorporate fault detection to diagnose debris in the flow path. The clear cycle can be installed as software in a ventilation device.

54 Claims, 9 Drawing Sheets

U.S. PATENT DOCUMENTS

| | | |
|---|---|---|
| 5,647,351 A | 7/1997 | Weissman et al. |
| 5,662,099 A | 9/1997 | Tobia et al. |
| 5,685,296 A | 11/1997 | Zdrojkowski et al. |
| 5,704,345 A | 1/1998 | Berthon-Jones |
| 5,803,065 A | 9/1998 | Zdrojkowski et al. |
| 5,823,187 A | 10/1998 | Estes et al. |
| 5,860,418 A | 1/1999 | Lundberg |
| 5,868,133 A | 2/1999 | DeVries et al. |
| 5,881,717 A | 3/1999 | Isaza |
| 5,881,723 A * | 3/1999 | Wallace et al. ........ 128/204.21 |
| 5,901,704 A | 5/1999 | Estes et al. |
| 5,904,141 A | 5/1999 | Estes et al. |
| 5,937,855 A | 8/1999 | Zdrojkowski et al. |
| 5,970,975 A | 10/1999 | Estes et al. |
| 6,024,087 A | 2/2000 | Kersey et al. |
| 6,029,664 A | 2/2000 | Zdrojkowski et al. |
| 6,164,276 A | 12/2000 | Bathe et al. |
| 6,220,244 B1 | 4/2001 | McLaughlin |
| 6,253,765 B1 | 7/2001 | Hognelid et al. |
| 6,279,574 B1 | 8/2001 | Richardson et al. |
| 6,299,581 B1 | 10/2001 | Rapoport et al. |
| 6,360,741 B2 | 3/2002 | Truschel |
| 6,363,270 B1 | 3/2002 | Colla et al. |
| 6,369,838 B1 | 4/2002 | Wallace et al. |
| 6,390,091 B1 * | 5/2002 | Banner et al. ......... 128/204.21 |
| 6,397,841 B1 | 6/2002 | Kenyon et al. |
| 6,425,395 B1 | 7/2002 | Brewer et al. |
| 6,539,940 B2 | 4/2003 | Zdrojkowski et al. |
| 6,584,973 B1 | 7/2003 | Biondi et al. |
| 6,591,834 B1 | 7/2003 | Colla et al. |
| 7,270,126 B2 * | 9/2007 | Wallace et al. ........ 128/202.22 |

FOREIGN PATENT DOCUMENTS

| | | |
|---|---|---|
| EP | 0621056 A1 | 10/1994 |
| EP | 0656216 A2 | 6/1995 |
| GB | 2281513 | 3/1995 |
| WO | WO 87/02898 | 5/1987 |
| WO | WO 96/03174 | 2/1996 |
| WO | WO 96/11717 | 4/1996 |
| WO | WO 97/28838 | 8/1997 |
| WO | WO 98/41268 | 9/1998 |

* cited by examiner

CLEAR CYCLE FOR VENTILATION DEVICE

CROSS REFERENCE TO PRIORITY APPLICATION

The present application claims the benefit of U.S. Provisional Patent Application No. 60/503,897 filed Sep. 22, 2003, the content of which is incorporated herein by reference in its entirety.

BACKGROUND OF THE INVENTION

1. Field of the Invention

The present invention relates to ventilation devices, and in particular, ventilation devices including a patient interface in fluid communication with a flow generator via a conduit.

2. Description of Related Art

Ventilation devices such as non-invasive positive pressure ventilation (NIPPV) and continuous positive airways pressure (CPAP) devices function to supply a patient with a supply of clean breathable gas (usually air, with or without supplemental oxygen) at a prescribed pressure or pressures at appropriate times during the patient's breathing cycle.

An example of such a ventilation device is the AutoSet®T device (ResMed Ltd., Australia), which may be used for treating sleep disordered breathing, such as Obstructive Sleep Apnea (OSA), as described in U.S. Pat. No. 5,704,345 (Berthon-Jones).

One problem of such devices is that debris and/or water condensate can enter a flow path of the ventilation device, which typically includes a flow generator in fluid communication with a patient interface via a conduit. The patient may attempt to use the ventilation device, despite the presence of the debris in the flow path of the ventilation device, because the patient may not be able to determine whether debris is present in the flow path prior to use.

The debris can be of such a nature that its presence does not substantially affect the flow characteristics of the ventilation device. Debris that does not substantially affect the flow characteristics of the ventilation device can easily go undetected. In use, the debris can travel along the flow path into the patient's airways. The debris can be of such a nature that it lodges in the flow path, affecting flow characteristics and partially or completely blocking flow from the ventilation device to the patient. Therefore, there is a need in the prior art for an improved apparatus and a method of performing a clear cycle with the apparatus to increase patient comfort and safety prior to treatment.

SUMMARY OF THE INVENTION

It is an aspect of the present invention to provide a clear cycle for a ventilation device and, in another form, a clear cycle with fault detection for a ventilation device which improves patient comfort and safety prior to treatment.

Accordingly, one embodiment of the present invention provides a method of performing a clear cycle in a ventilatory assistance apparatus including a flow generator in fluid communication with a patient interface in a flow path. The method includes examining a plurality of operational parameters, determining whether the flow generator should generate flow based on at least one of the plurality of operational parameters, warning the patient to avoid interfacing with the patient interface of the ventilation device prior to generating the flow, and operating the flow generator to generate the flow in accordance with at least one of the plurality of operational parameters.

In another embodiment, the present invention provides a ventilatory assistance apparatus including a flow generator in fluid communication with a patient interface in a flow path, configured to perform a clear cycle. The ventilatory assistance apparatus includes a data storage configured to store a plurality of operational parameters, a controller configured to determine whether the flow generator should generate flow based on at least one of the plurality of operational parameters, and a display configured to warn the patient to avoid interfacing with the patient interface of the ventilation device prior to the controller determining that the flow generator should generate the flow, wherein the controller instructs the flow generator to generate the flow in accordance with at least one of the plurality of operational parameters.

In yet another embodiment, the present invention provides a computer-readable medium carrying one or more instructions for performing a clear cycle in a ventilatory assistance apparatus including a flow generator in fluid communication with a patient interface in a flow path. The instructions include examining a plurality of operational parameters, determining whether a flow should be generated based on at least one of the plurality of operational parameters, warning the patient to avoid interfacing with the patient interface of the ventilation device prior to generating the flow, and operating the flow generator to generate the flow in accordance with at least one of the plurality of operational parameters.

In yet another embodiment, the present invention provides a computer data signal embodied in a carrier wave including one or more instructions for performing a clear cycle in a ventilatory assistance apparatus including a flow generator in fluid communication with a patient interface in a flow path. The instructions include examining a plurality of operational parameters, determining whether a flow should be generated based on at least one of the plurality of operational parameters, warning the patient to avoid interfacing with the patient interface of the ventilation device prior to generating the flow, and operating the flow generator to generate the flow in accordance with at least one of the plurality of operational parameters.

These and other aspects of the invention will be described in or apparent from the following detailed description of preferred embodiments.

DETAILED DESCRIPTION OF PREFERRED EMBODIMENTS

Figure 1:
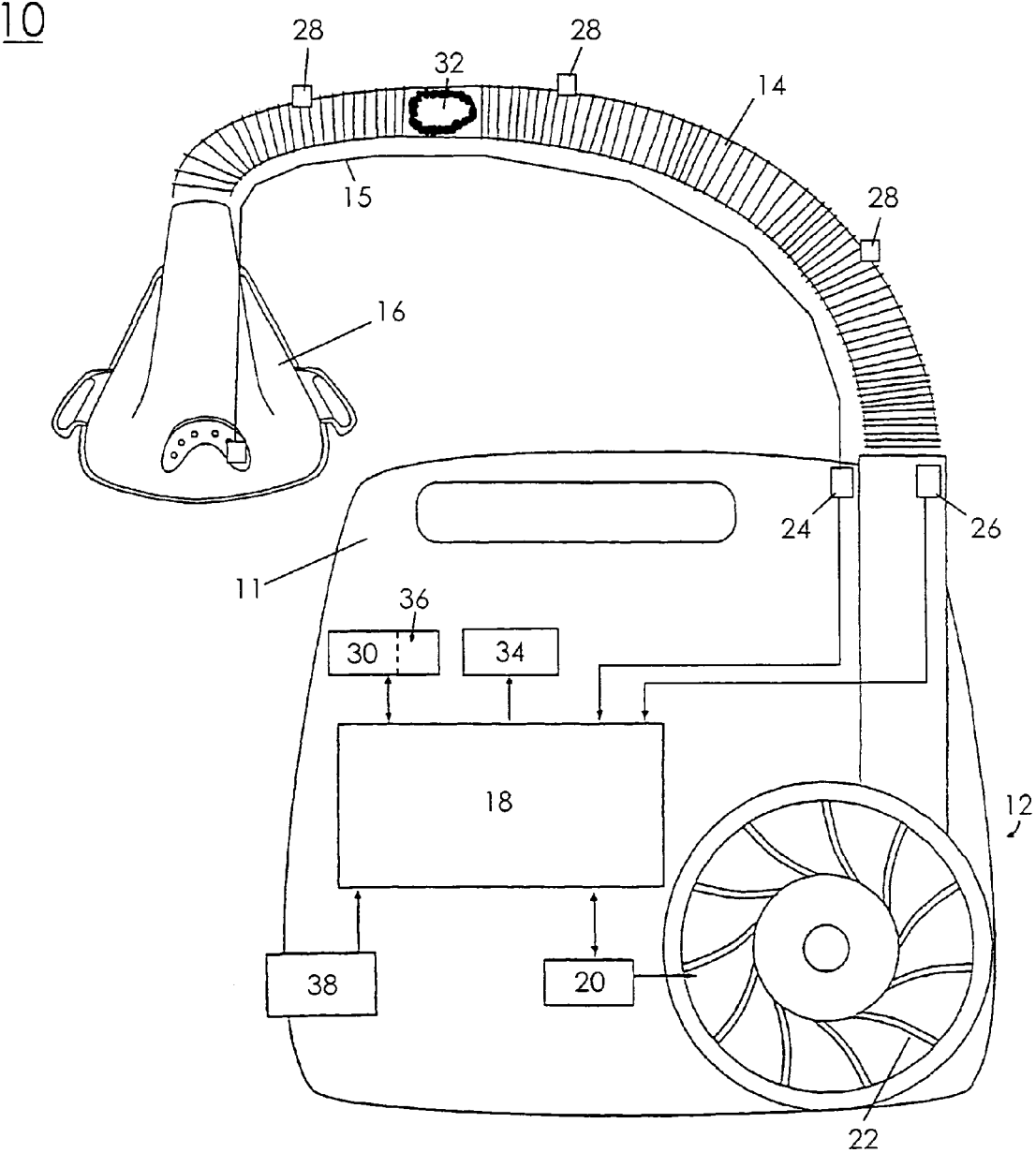
FIG. 1 is a top schematic view of a ventilation device configured with a clear cycle.

As shown in FIG. 1, a ventilation device 10 typically includes a flow generator 12 and an air delivery conduit 14 connecting the output of the flow generator 12 to a patient interface 16. The flow generator 12 develops a flow of breathable gas, which flows along a flow path formed by the flow generator 12, the conduit 14 and the patient interface 16. The patient interface 16 delivers the flow of breathable gas from the flow generator 12 into the patient's airways.

Typically, the patient interface 16 can be a mask. The mask can be a nasal mask, a mouth mask, a nasal and mouth mask in combination, a full face mask, nasal pillows or nasal prongs. Any reference to a patient interface 16 is to be understood as embracing all of the above-described forms of patient interfaces.

The ventilation device 10 can include a controller 18, a motor 20, and an impeller 22 rotatably connected to the motor 20. The controller 18 can direct the motor 20 via appropriate signal lines to operate the impeller 22 based on specific criteria and thereby develop a flow of breathable gas. The ventilation device 10 can include data storage 30 for storing various operational parameters 36. It is contemplated that data storage 30 can be incorporated into controller 18. The ventilation device 10 may also include a display 34 and a menu interface 38 connected to the controller 18, for communication with a patient or other user. For example, the display 34 can be an LCD readout and the menu interface 38 can be a keypad. The ventilation device 10 can include a buzzer and/or a speaker (not shown) to provide an audible warning and/or informative instructions.

The controller 18, based on the stored operational parameters 36, can direct the flow generator 12 to perform a clear cycle upon startup of the ventilation device 10, prior to the patient wearing the patient interface 16, by generating a flow which can be capable of displacing loose debris 32 or water condensate in the flow path of the ventilation device 10. Clearing the flow path of loose debris 32 prior to patient use can improve patient safety because the debris 32 can be discharged to the environment prior to use, and not into the patient's airways during use.

A clear cycle can represent an economical solution to the problem of debris and/or water condensate in the flow path prior to use by a patient, because the clear cycle can be implemented with appropriate software, using existing hardware provided in a typical ventilation device.

Ventilation device 10 can be used in a non-clinical setting such as the patient's home. Typically the patient is untrained to detect debris 32 in the flow path of the ventilation device 10. Use of the ventilation device 10 with debris 32 in the flow path can result in non-optimal treatment administered to the patient. It is possible that, after a period of non-use, debris 32 can be introduced inadvertently into the flow generator 12, conduit 14 or patient interface 16. For example, debris 32 can be a rodent or insect present in the flow path, and/or a rodent or insect can contaminate the flow path of the ventilation device 10 with debris 32, without the patient's knowledge. When the patient attempts to use the ventilation device 10, the flow generator 12 can force the debris 32 into the patient's airways, or the debris 32 can prevent the ventilation device 10 from producing sufficient airflow for treatment.

The ventilation device 10 can be arranged to perform a clear cycle to displace debris 32 from the ventilation device 10, and performing the clear cycle can allow the ventilation device 10 to provide fault diagnosis information understandable to those without clinical or technical skills. One embodiment of the clear cycle can be a simplified process which operates the flow generator 12 for a predetermined duration of time prior to patient use. Another embodiment of the clear cycle can be a process which checks for fault conditions during the operation of the flow generator 12 for a predetermined duration of time prior to patient use.

In use, pressure can develop along the flow path, which can be related to the flow impedance characteristics of the flow path. For example, during operation of the flow generator 12, pressure in the flow path can increase when the patient wears the patient interface 16, because the patient wearing the patient interface 16 increases flow impedance. Debris 32 in the conduit 14 can increase flow impedance as well. Sensors can be used to differentiate between an increase in flow impedance caused by debris 32 and an increase in flow impedance caused by the patient wearing the patient interface 16.

The ventilation device 10 can include a sensor 24 connected to the controller 18 for sensing pressure in the flow path. As illustrated, the sensor 24 can be arranged within the housing 11 of the ventilation device 10. With such an arrangement of sensor 24 in the housing 11, an auxiliary conduit 15 can be arranged in fluid communication with the patient interface 16 to communicate the pressure at the patient interface 16 to the sensor 24 in the housing 11.

Alternatively, the sensor 24 can be arranged at the patient interface 16 to directly sense the pressure at the patient interface 16. With such an arrangement, a wire or other signal line can be arranged to carry a signal indicative of the sensed pressure from the sensor 24 at the patient interface 16 to the controller 18, rather than using the auxiliary conduit 15 to communicate pressure.

The ventilation device 10 can include a sensor 26 connected to the controller 18 for sensing pressure in the flow path upstream of the pressure in the flow path sensed by sensor 24. The sensor 26 can measure pressure at the flow generator 12. It is contemplated that a plurality of additional sensors 28 can be arranged along the conduit 14 to sense pressure along the flow path within the conduit 14.

The controller 18 can obtain the overall pneumatic performance, or air delivery, of the ventilation device 10 during an auto pressure calibration, for example. Typical pneumatic performance criteria can be factory set in the controller 18. A clear cycle process 200, illustrated in FIG. 4, may be used to check the overall pneumatic performance of the ventilation device 10 (at step 212, for example), and can compare the pneumatic performance of the ventilation device 10 during the clear cycle process 200 with the calibrated or typical pneumatic performance previously obtained.

At a given rotational speed of the motor 20, and a given air delivery circuit pneumatic impedance, the flow generator will deliver gas at a particular pressure. An acceptable range of measured pressure values at the output of the flow generator 12 and at the patient interface 16 may be calculated for a given set of conditions, which can be defined by upper and lower characteristic curves (i.e., "high" and "low" pressures, for example). The output of the flow generator 12 may be increased to maintain an acceptable output pressure as a response to increased impedance. Pressure outside an acceptable range may be indicative of debris 32 lodged in the air delivery circuit.

During flow generation, pressure values sensed by the plurality of sensors 24, 26, 28 are measured and compared with acceptable ranges of measured pressure values. When the values fall outside of the acceptable ranges, corrective action can be taken. For example, the controller 18 can issue a warning and/or shut down the ventilation device 10. An error message can be displayed on display 34, an audible warning can be given (for example, an alarm and/or informative verbal instructions), and appropriate action can be taken (e.g., the ventilation device 10 can be shut down). Accordingly, the patient can be informed of a problem, when the patient is not qualified to diagnose that there is a problem with the ventilation device 10.

In use, controller 18 can monitor the pressure at the patient interface 16 indicated by the pressure sensor 24 and can monitor the pressure indicated at the flow generator 12 by the pressure sensor 26. For example, controller 18 can monitor low pressure at the patient interface 16 and high pressure at the flow generator 12, which can be an indication of flow blockage caused by debris 32. Flow blockage can cause pressure to increase upstream of the flow blockage and decrease downstream of the flow blockage. The controller 18 can accordingly respond to the sensed pressure conditions. For example, the controller 18 can shut down the motor 20, or the controller 18 can instruct the flow generator 12 to generate flow for a duration of time to force debris 32 out of the flow path. When flow blockage is caused by debris 32 that cannot be dislodged, the motor 20 can be disabled. The entire operation of the ventilation device 10 can be disabled until service can be performed. Such a mode can be termed the "service required" mode.

As described above, low pressure at the patient interface 16 and high pressure at the flow generator 12 is one of several conditions that the controller 18 can identify. The controller 18 can also identify low pressure at both the patient interface 16 and the flow generator 12. Such a condition could indicate that the patient interface 16 is not being worn by the patient, or that the conduit 14 is disconnected from the flow generator 12, for example.

Additional sensors 28 can sense pressure along the conduit 14 to provide additional pressure readings at points along the conduit 14. The readings are provided to the controller 18. In the case where one additional sensor 28 is arranged within the conduit 14, the controller 18 can obtain a pressure reading corresponding to the location of the sensor 28 in the conduit 14. For example, the sensor 28 can be located mid-way between the patient interface 16 and the flow generator 12. The reading can be used to determine if a high, a normal, or a low pressure condition exists in the conduit 14, and can be used in conjunction with the readings from sensors 24 and 26 to more specifically identify the location of debris 32. For example, if sensors 26 and 28 (sensor 28 located mid-way between sensors 24 and 26) sense a high pressure, and sensor 24 senses a low pressure, debris 32 can be identified as being located between the patient interface 16 and sensor 28. If sensors 24 and 28 sense a low pressure, and sensor 26 senses a high pressure, debris 32 can be identified as being located between the flow generator 12 and sensor 28. Determination of where debris 32 could potentially be located can be provided for diagnostic purposes. Of course, more than one sensor 28 (three sensors 28 as shown in FIG. 1) can be used to further increase the diagnostic resolution to better identify the location of blocking debris 32.

There may be a relationship between the pressures measured by sensors 24-28 such that acceptable ranges of the pressures can be determined for acceptable operation of the ventilation device 10. Debris 32 can cause unacceptable ranges of measured pressure, which can result in a fault condition. The clear cycle may diagnose a fault if the sensed parameters fall outside the acceptable range for an instant in time, or for some duration of time.

If diagnosis of debris 32 resulting in a fault condition occurs, the response can be one or more of the following: issuing a warning of the fault condition, recording a description of the fault condition, transmitting a warning and/or description of the fault condition to a remote location, adjusting operational parameters and switching between functional and stand-by or stop modes, or switching the device to a service-required mode.

Any reference to "operational parameters" is to be understood to relate to any form of data or state signal, sensor or actuator, and the mechanical and electrical functions of components elements/apparatus of the ventilation device 10. Any reference to clear cycle is understood to be implemented by hardware and/or software.

Advantageously, the clear cycle is implemented in software. In this case, no additional hardware is needed. The clear cycle can be implemented in a ventilation device 10 using appropriate computer readable storage media and/or via a transmission of computer readable instructions. For example, a magnetic or optical disk can be used, a serial, parallel or network interface can be used, and/or the internet can be used to implement embodiments of the present invention. Alternatively, the clear cycle can be implemented in hardware by storing instructions in a control module adapted for installation and/or retrofitting in an existing flow generator. The clear cycle process may be executed in conjunction with existing software. Aspects of exemplary embodiments of a clear cycle process are illustrated in the flow charts of FIGS. 2-7.

Upon startup of the ventilation device 10, the display 34 displays a Welcome Screen. After running any automatic processes upon startup, the display 34 then displays a Main Menu Options screen. When the Main Menu Options screen is displayed, the patient has the option of selecting various processes, including a setup process 100.

Figure 2A:
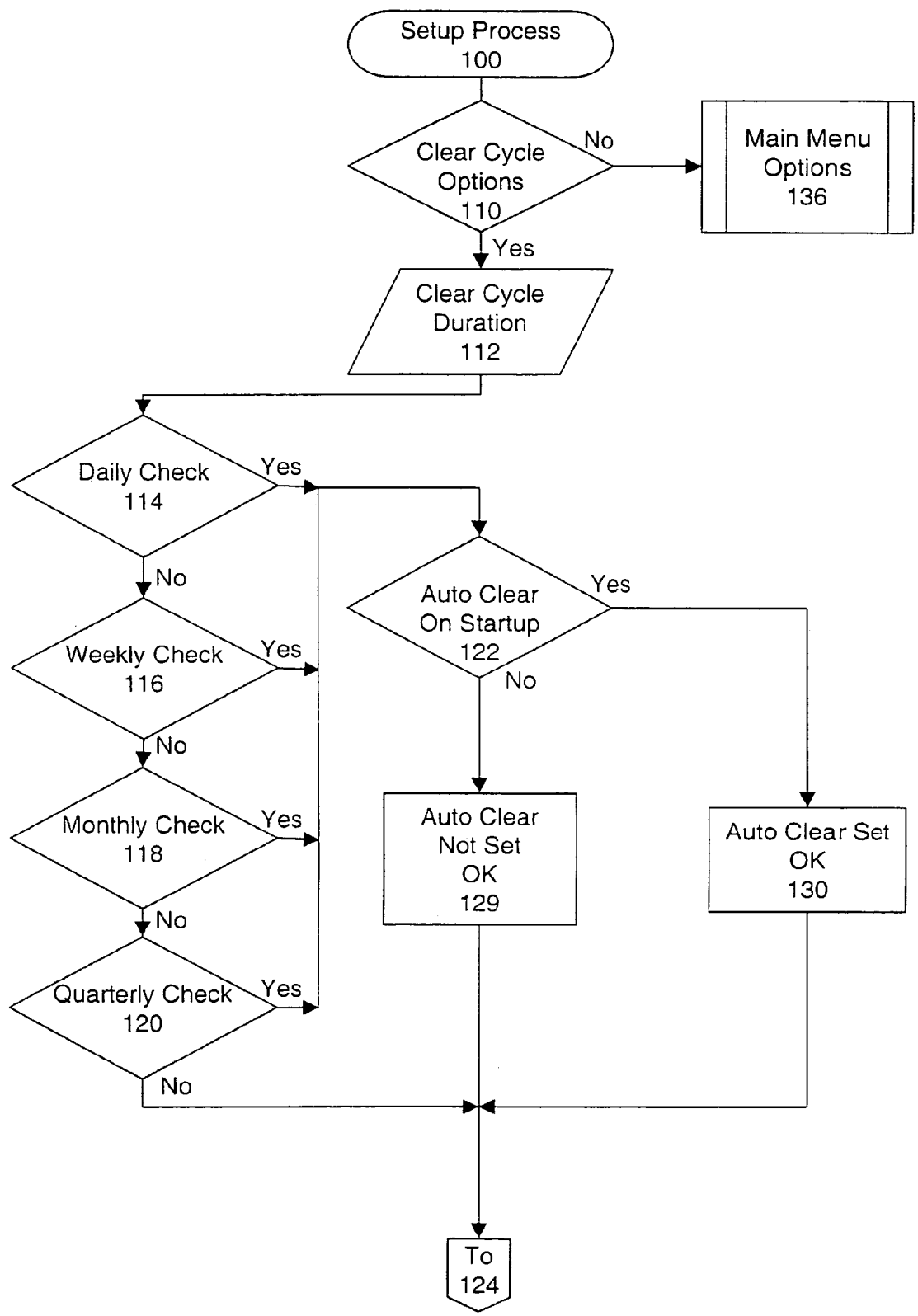
FIG. 2A is a first part of a flow chart of a setup process.

FIG. 2A illustrates a first part of the setup process 100. The setup process 100 allows a patient to set various operational parameters 36 to customize the operation of the clear cycle. It is understood that, besides the patient, a user such as a technician or health professional can interface with the ventilation device 10 to set the operational parameters 36.

The operational parameters 36 can be set to acceptable values prior to clinical use, corresponding to the preferences of a particular patient or an average setting representative of the most common typical patient preferences. The setup process 100 can be selected from the options menu of the ventilation device 10. Even if the clear cycle is set to automatically run at startup, the setup process 100 is always available to reconfigure clear cycle preferences via the operational parameters 36.

At step 110, the controller 18 prompts the patient via display 34 to choose whether to set the clear cycle options. Selecting "No" via the menu interface 38 exits from the setup process 100 to the main menu options 136. Selecting "Yes" at step 110 causes the setup process 100 to proceed to step 112 and the patient is prompted to specify the duration of the clear cycle, preferably in seconds. The patient can enter the preferred duration of the clear cycle in seconds via the menu interface 38, typically a keypad. Ranges of the duration can fall within 5-20 seconds, for example.

The patient is then prompted to indicate to the controller 18 whether to run the clear cycle, or provide a reminder to manually run the clear cycle, daily at step 114, weekly, at step 116, monthly, at step 118, or quarterly, at step 120. Selecting "Yes" at one of steps 114-120 can cause the controller 18 to store corresponding operational parameters 36 in data storage 30 indicating how often to run the clear cycle or provide a reminder, and proceed to step 122, where the patient can select whether to automatically run the clear cycle upon startup. If the patient chooses at step 122 not to run the clear cycle automatically upon startup, the controller 18 can store a setting in data storage 30 which indicates that the controller 18 should not automatically run the clear cycle (i.e., not perform an auto clear) upon startup. At step 129 the patient is then prompted to acknowledge that auto clear is not set by selecting "OK." Of course, the patient has the option of manually running a clear cycle if auto clear is not set (see, for example, FIG. 3A, step 164).

If the patient chooses at step 122 to run the clear cycle automatically upon startup, the controller 18 can store a setting in data storage 30 which indicates that the controller 18 should perform an auto clear upon startup. At step 130 the patient is then prompted to acknowledge that auto clear is set by selecting "OK." After step 129 or 130, or step 120 if the patient chooses not to specify an interval for running the clear cycle or displaying a reminder to run the clear cycle at steps 114-120, the setup process 100 proceeds to step 124.

Figure 2B:
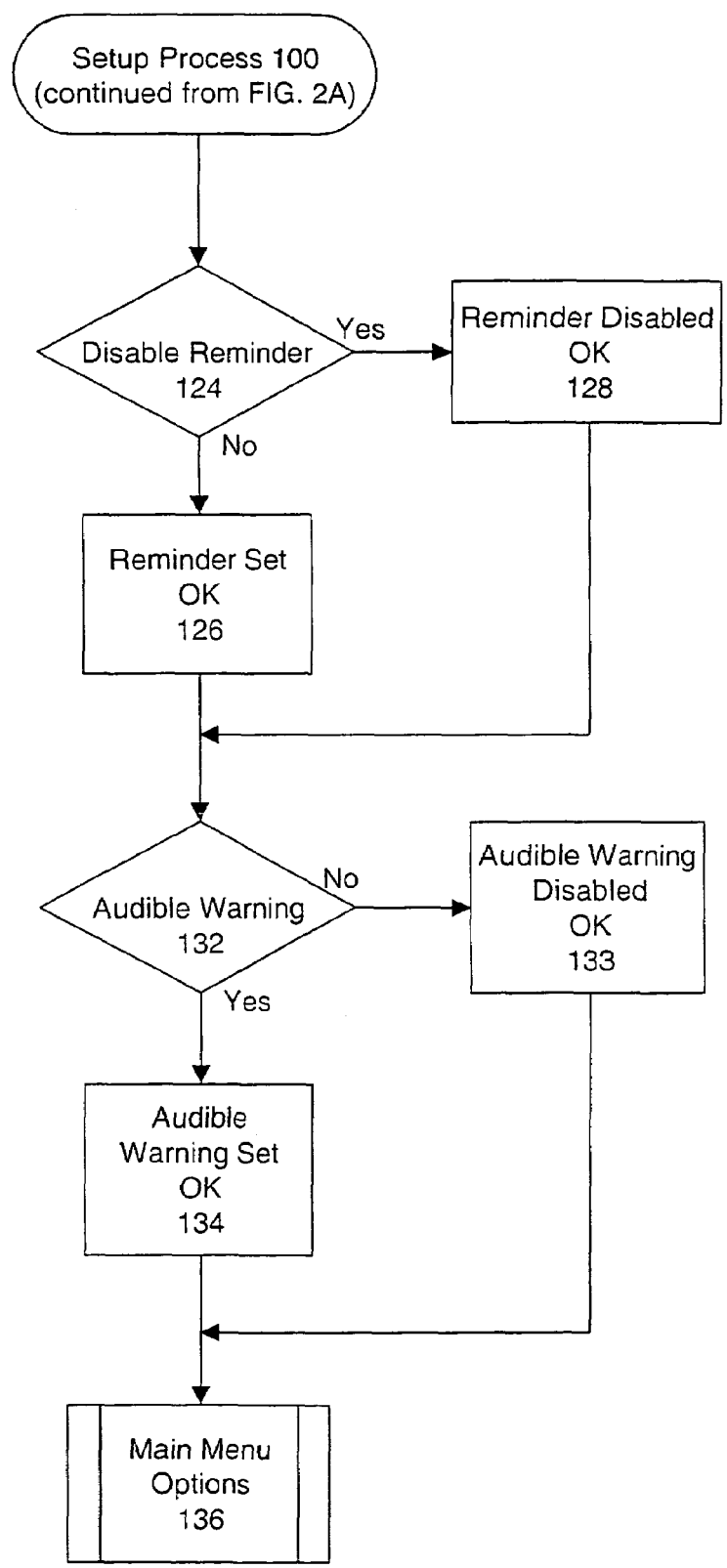
FIG. 2B is a second part of the flow chart of the setup process.

FIG. 2B illustrates a second part of the setup process 100. At step 124, the patient can choose to set or disable the clear cycle reminder at steps 126 or 128, respectively. The controller 18 can store operational parameters 36 corresponding to the setting of the reminder in data storage 30, and request acknowledgement from the patient by selecting "OK" in steps 126 or 128.

The patient is further prompted to determine whether to set an audible warning at step 132. If the patient decides not to set the audible warning, the audible warning is disabled at step 133, and the patient is prompted to acknowledge that the audible warning is disabled by selecting "OK." The controller 18 then exits to main menu options at step 136. If the patient decides to set an audible warning at step 132, the controller 18 sets the corresponding operational parameter 36, requests acknowledgement at step 134, and exits to the main menu options at step 136.

Figure 3A:
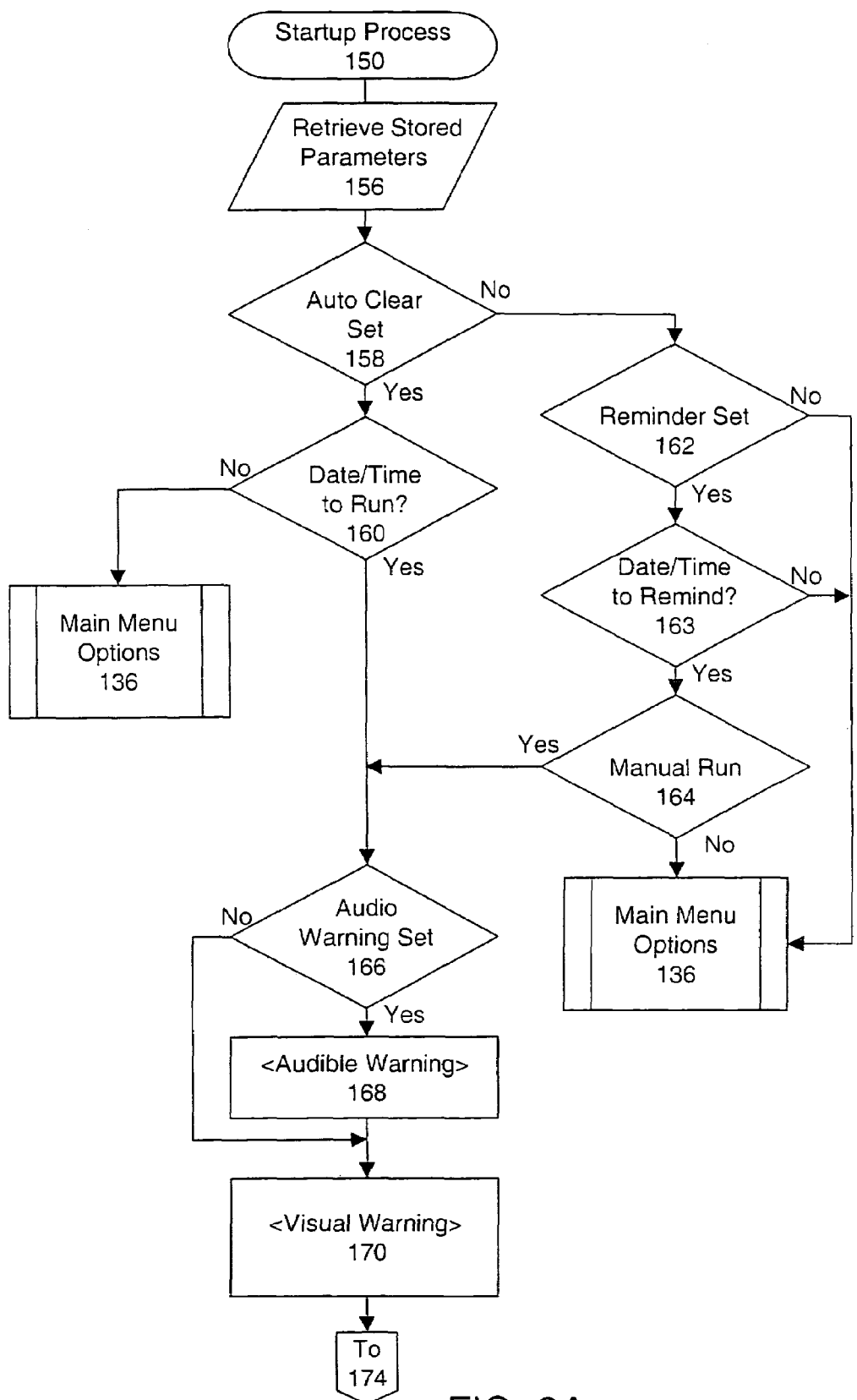
FIG. 3A is a first part of a flow chart of a startup process.

FIG. 3A illustrates a first part of an embodiment of a ventilation device 10 startup process 150. Upon startup of the ventilation device 10, the controller 18 of the ventilation device 10 can retrieve the stored operational parameters 36 from the data storage 30 of the controller 18 at step 156. The controller 18 can retrieve stored operational parameters 36 obtained during the setup process 100. For example, the controller 18 can retrieve the operational parameters 36 corresponding to the duration of the clear cycle obtained in step 112, how often the clear cycle should be run obtained in any one of steps 114-120, whether to run the clear cycle automatically upon startup obtained in step 122, whether a clear cycle reminder prompt should be disabled obtained in step 124, and/or whether to provide an audible warning obtained in step 132.

At step 158 the controller 18 examines one or more of the operational parameters 36 corresponding to whether the auto clear parameter is set. If auto clear is set, the controller 18 proceeds to step 160. The controller 18 can include an internal timer and/or real-time clock for checking the time since the last clear cycle run and/or for checking the current time/date. Additionally, an external signal can be used. At step 160, the controller 18 checks the timer to determine whether it is time to run the clear cycle. If at step 160 it is not time to run the clear cycle, the startup process 150 exits to the main menu options 136.

If at step 158 the controller 18 determines that auto clear is not set, the startup process 150 proceeds from step 158 to step 162. At step 162 the controller 18 determines whether a clear cycle reminder is set based on the stored operational parameters 36. If the clear cycle reminder is not set, the startup process 150 exits to the main menu options at step 136. If the clear cycle reminder is set, the controller 18 determines at step 163 whether it is time to remind the patient to perform a manual clear cycle. The determination can be made based on an internal timer, a real time clock, and/or an external signal. If it is not time to provide a reminder, the startup process 150 exits to the main menu options at step 136. If it is time to remind the patient, the patient is prompted at step 164 to determine whether to run the clear cycle manually. If the patient chooses not to run the clear cycle manually, the patient is prompted with the main menu options at step 136.

If the patient chooses at step 164 to manually run the clear cycle, or if the controller 18 determines at step 160 to run the clear cycle, the startup process 150 proceeds to step 166, at which step the controller 18 determines whether the audio warning has been set based on the stored operational parameters 36. If the audio warning has been set, the controller 18 instructs an alarm or speaker (not shown) to issue an audible warning at step 168. The audible warning can be a beep and/or arousing/informative voice prompt. If the audio warning is not set, the startup process 150 proceeds from step 166 to step 170 without providing an audible warning. At step 170, the controller 18 instructs the display 34 to display a visual warning message. For example, the display 34 displays an informative warning to the patient that the clear cycle is about to start and that the patient should not wear the patient interface.

Figure 3B:
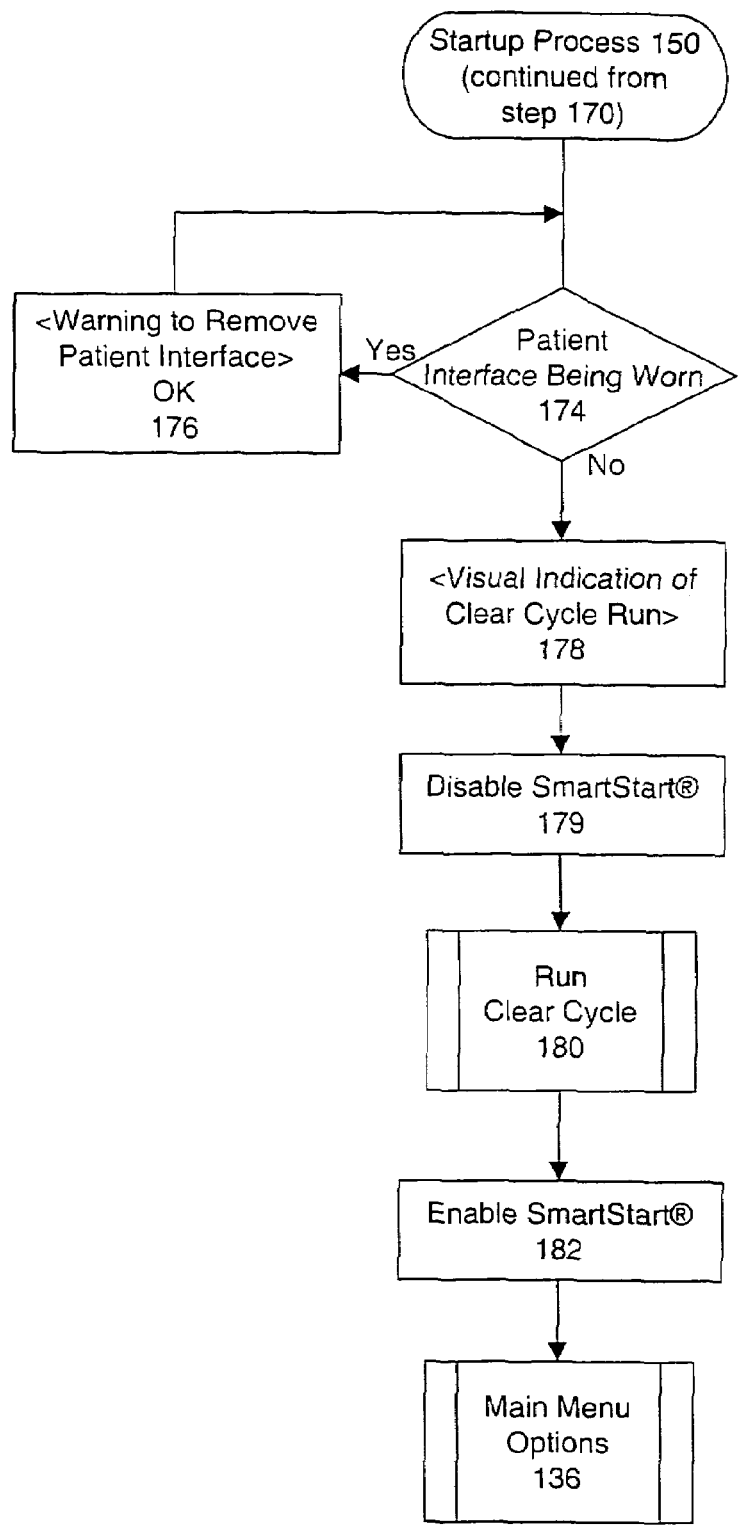
FIG. 3B is a second part of the flow chart of the startup process.

FIG. 3B illustrates a flow chart of the second part of the startup process 150. At step 174, the controller 18 determines whether the patient is wearing the patient interface 16. The ventilation device 10 may be automatically started when the patient dons the patient interface 16 and may be automatically stopped when the patient removes the patient interface 16. The controller 18 can be programmed to determine whether the patient interface 16 is being worn, e.g., by use of appropriate pressure and/or proximity sensors.

The controller 18 can use additional sensors (not shown) installed in the patient interface 16 to determine whether the patient interface 16 is worn. For example, the patient interface 16 can have a sensor to sense contact between facial cushions of the patient interface 16 and the patient's face, and/or the patient interface 16 can have a sensor to sense heat from the patient's face.

If the controller 18 determines at step 174 that the patient is wearing the patient interface 16, the controller 18 immediately halts flow from the flow generator 12 and instructs the display 34 to display a warning message to remove the patient interface at step 176. An audible warning can be generated as well. At step 176, the controller 18 waits for the patient to remove the patient interface 16 and acknowledge the warning message by selecting "OK." Upon acknowledgment, the startup process 150 returns to step 174 where the controller 18 again determines whether the patient is wearing the patient interface 16.

After confirming that the patient is not wearing the patient interface 16, the startup process 150 proceeds to step 178, where the controller 18 for example displays via display 34 a message that the clear cycle is currently running and that the patient should please wait.

Because it is necessary to operate the ventilation device 10 during the clear cycle while the patient interface 16 is not worn, it is necessary to disable SmartStart® during the clear cycle. At step 179, the controller 18 disables SmartStart® (if applicable). By disabling SmartStart® at step 179, the controller 18 is able to operate the flow generator 12 even though the patient is not wearing the patient interface 16, so the clear cycle can be run. At step 180, the clear cycle is run (see FIG. 4). After running the clear cycle at step 180, the startup process 150 proceeds to step 182, where the controller 18 enables SmartStart®. The startup process 150 ends and prompts the patient with the main menu options at step 136.

Figure 4:
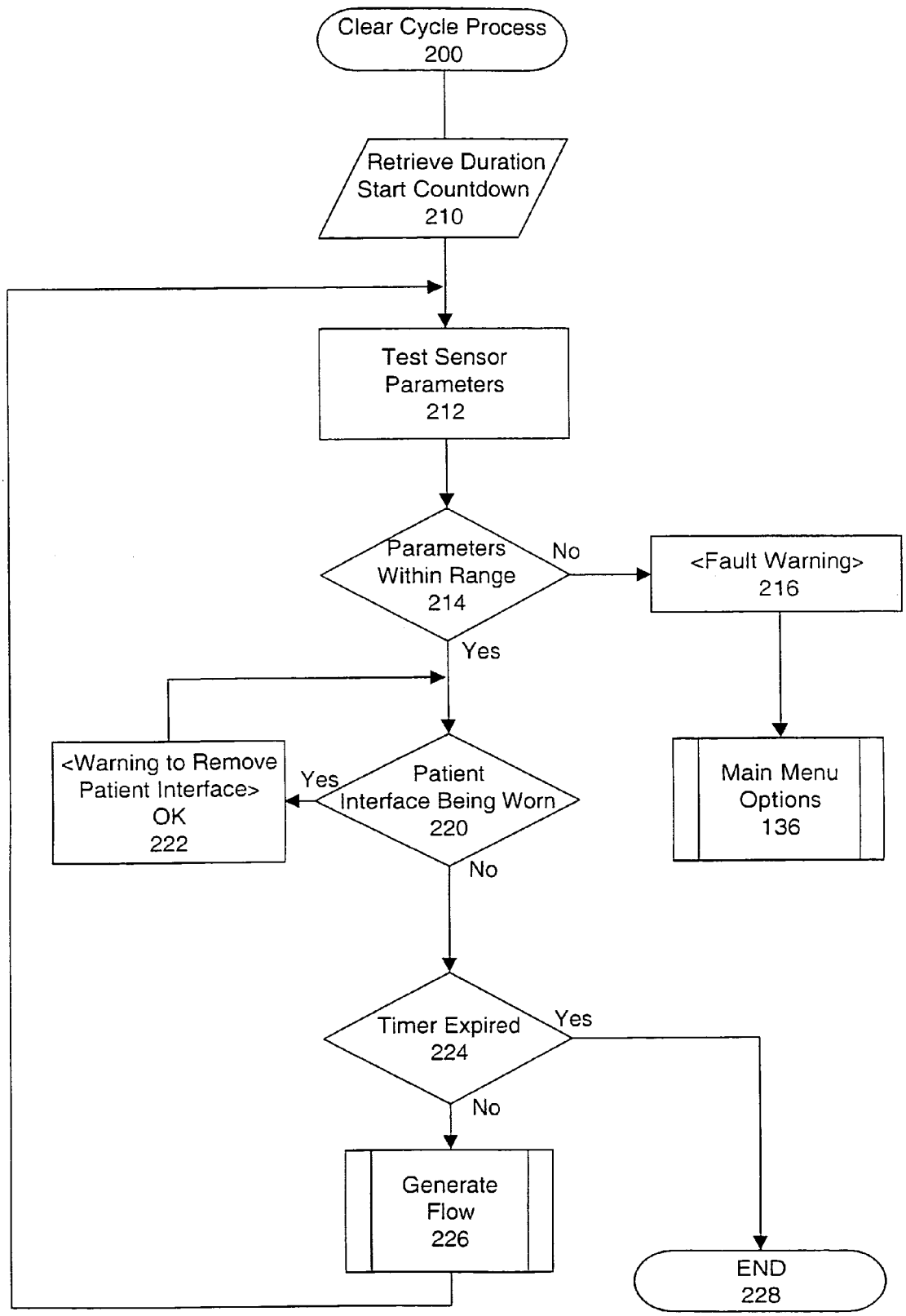
FIG. 4 is a flow chart of a clear cycle process.

FIG. 4 illustrates an embodiment of the clear cycle process 200 called by step 180 of the startup process 150 shown in FIG. 3B. At step 210, the controller 18 retrieves from the stored operational parameters 36 the duration of the clear cycle, obtained for example in step 112 of the setup process 100. The controller 18 then starts a timer countdown of this duration and proceeds to step 212. At step 212, the controller 18 tests the sensor parameters from the sensors, which can include sensors 24, 26, and 28 (if applicable), and proceeds to step 214.

At step 214, the controller 18 determines whether the sensor parameters are within a valid range. For example, a valid range of the sensor parameters could be a normal pressure at the patient interface 16 sensed by the sensor 24, and a normal pressure at the output of the flow generator 12 sensed by the sensor 26. In this case, a low pressure would be below about 0-2 cm $H_2O$, a high pressure would be above 15-20 cm $H_2O$, and a normal pressure would be between 0-2 cm $H_2O$ and 15-20 cm $H_2O$. An example of an invalid range of the sensor parameters would be a low pressure at the patient interface 16 sensed by sensor 24, and a high pressure at the output of the flow generator 12 sensed by sensor 26.

The controller 18 can calculate an acceptable range of measured pressure values for a given set of conditions. For example, a pressure obtained from sensor 24 can have an upper value limit corresponding to the safety of the patient during treatment, e.g., 15-20 cm $H_2O$. Additionally, the pressure obtained from sensor 26 can have an upper value corresponding to a predetermined range of values within which the flow generator 12 can safely operate.

In a case where the sensor parameters are not within a valid range at step 214, the controller 18 determines that a fault has been detected, and the clear cycle process 200 proceeds from step 214 to step 216. The controller 18 can issue a visual warning via display 34, issue an audible warning, shut down the ventilation device 10, and/or take appropriate fault handling actions, depending upon the severity of the fault detected. For example, the controller 18 can send a signal remotely via the internet indicating that service is required.

It is possible in the event of particular fault conditions for the controller 18 to maintain operation of the motor 20 for a duration of time to dislodge debris 32. In the case that debris 32 cannot be dislodged, which results in the pressure sensed at the sensor 26 increasing over a duration of time, the controller 18 can shut down the motor 20 and enter the service required mode, for example. The clear cycle process 200 can then exit to the main menu options 136.

If the controller 18 determines that the sensor parameters are within a valid range at step 214, the clear cycle process 200 proceeds to step 220, where the controller 18 determines whether the patient is wearing the patient interface 16. If the controller 18 determines that the patient is wearing the patient interface 16, the patient is prompted at step 222 to remove the patient interface 16 and indicate that it is "OK" to continue.

After ensuring that the patient is not wearing the patient interface at steps 220-222, the clear cycle process 200 proceeds to step 224, where the controller 18 checks whether the duration timer countdown has expired. If the countdown has not expired, the clear cycle process 200 proceeds to step 226. At step 226, the controller 18 instructs the flow generator 12 to generate flow. The pressure and flow rate of the flow generated can vary based on settings factory pre-set or based on the operational parameters 36 set via the main menu options 136, for example. The clear cycle process 200 then proceeds to step 212 to repeat applicable steps 212-226. If the controller 18 determines at step 224 that the countdown timer has expired, the clear cycle process 200 ends at step 228 and flow control returns to step 182 of the startup process 150.

The flow rate generated by the flow generator 12 can have an upper limit that can correspond to a flow rate resulting in a pressure at the patient interface 16 of, for example, 15-20 cm $H_2O$ if the patient interface was being worn by a patient. By limiting the maximum flow rate of the flow generator 12 during the clear cycle process 200, the patient can be protected in cases where the patient inadvertently wears the patient interface 16 while a maximum flow rate is being delivered to the patient interface 16. A pressure of 15-20 cm $H_2O$ can be used because, depending on the patient and the effect the pressure has on the patient, delivering a flow at a pressure of 15-20 cm $H_2O$ typically does not damage the patient's airways.

It is contemplated that the flow generator 12 can deliver a maximum flow rate during the clear cycle that could potentially result in a pressure at the patient interface 16 greater than 15-20 cm $H_2O$ if the patient interface 16 is worn, provided that in the event the patient interface 16 is worn, flow delivery is immediately halted. The controller 18 can constantly monitor whether the patient interface is worn. For example, the controller 18 can monitor output of the sensor 24 corresponding to the pressure at the patient interface 16. A pressure at the patient interface 16 which exceeds a value of 15-20 cm $H_2O$, for example, can be indicative of the patient wearing the patient interface 16. The flow generator 12 can be shut down immediately to protect the patient if the controller determines that the patient interface 16 is worn. The determination whether the patient interface 16 is worn can be made based on the output of other sensors (not shown) such as heat sensors or pressure sensors in cushions of the patient interface 16 to detect the patient's face.

The flow generator 12 can deliver maximum flow rate for a duration, even though the sensor 26 which monitors the output of the flow generator 12 registers a high value, provided that the controller 18 determines that the patient interface 16 is not worn. The flow generator 12 can be operated at maximum flow rate for a duration sufficient to dislodge the debris 32, while ensuring that the patient interface 16 is not worn. It is contemplated that the duration of time that maximum flow rate is developed for dislodging debris 32 can be adjustable.

The plurality of operational parameters 36 are obtained and stored in data storage 30 of the ventilation device 10. Data storage 30 can include memory, disk, and/or other suitable storage devices. The operational parameters 36 can also be stored externally to the ventilation device 10. The preferences can be transmitted to and from a remote location via a public communication system such as the public telephone system or the internet. The preferences can be obtained and stored remotely. For example, the preferences can be sent from a doctor's office to the ventilation device 10 at a patient's home, and stored remotely at a data warehouse. Additionally, the setup process, startup process, and clear cycle process similarly can be updated to change, eliminate or incorporate new steps or otherwise improve the operation of the clear cycle.

Figure 5:
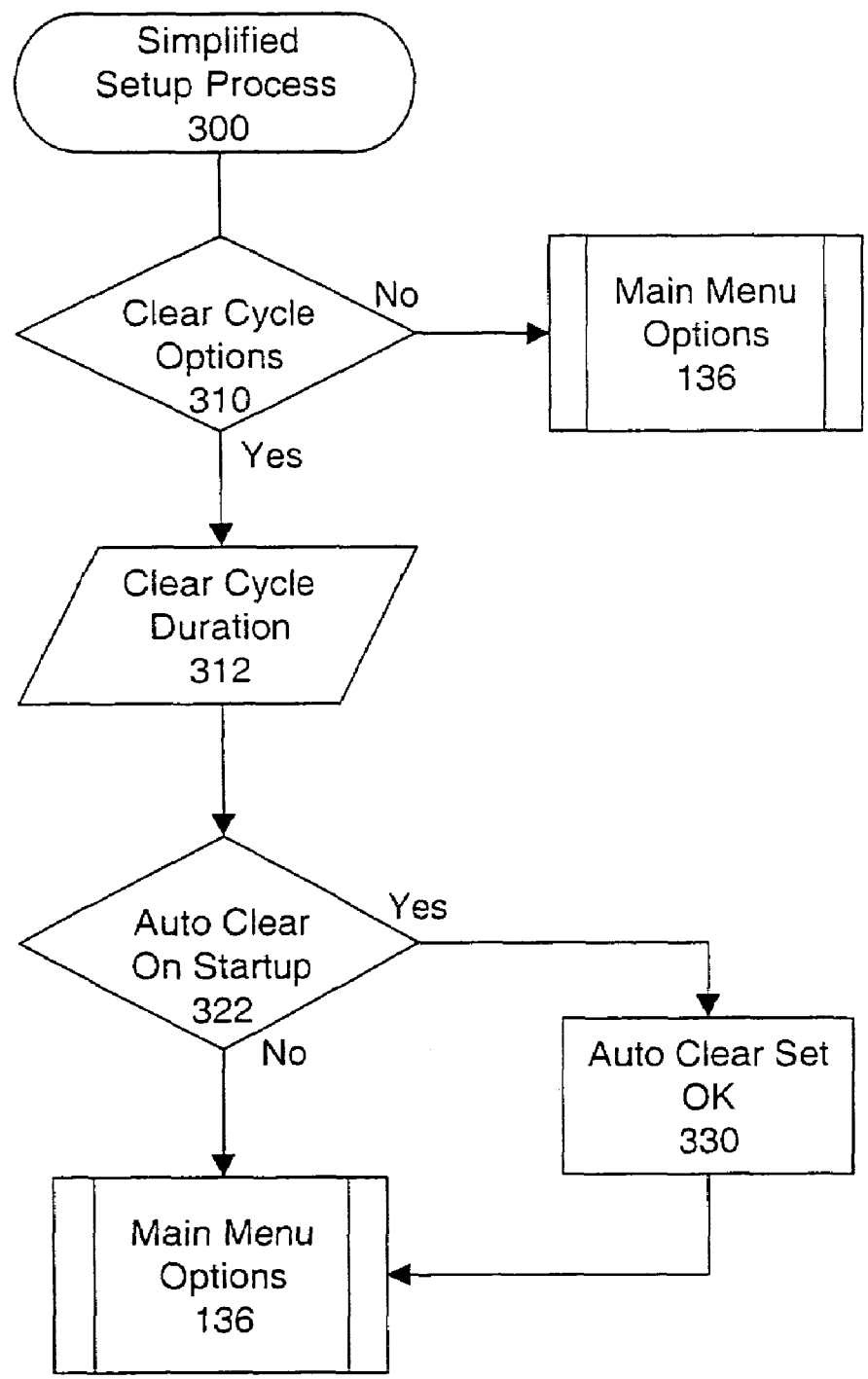
FIG. 5 is a flow chart of a simplified setup process.
Figure 6:
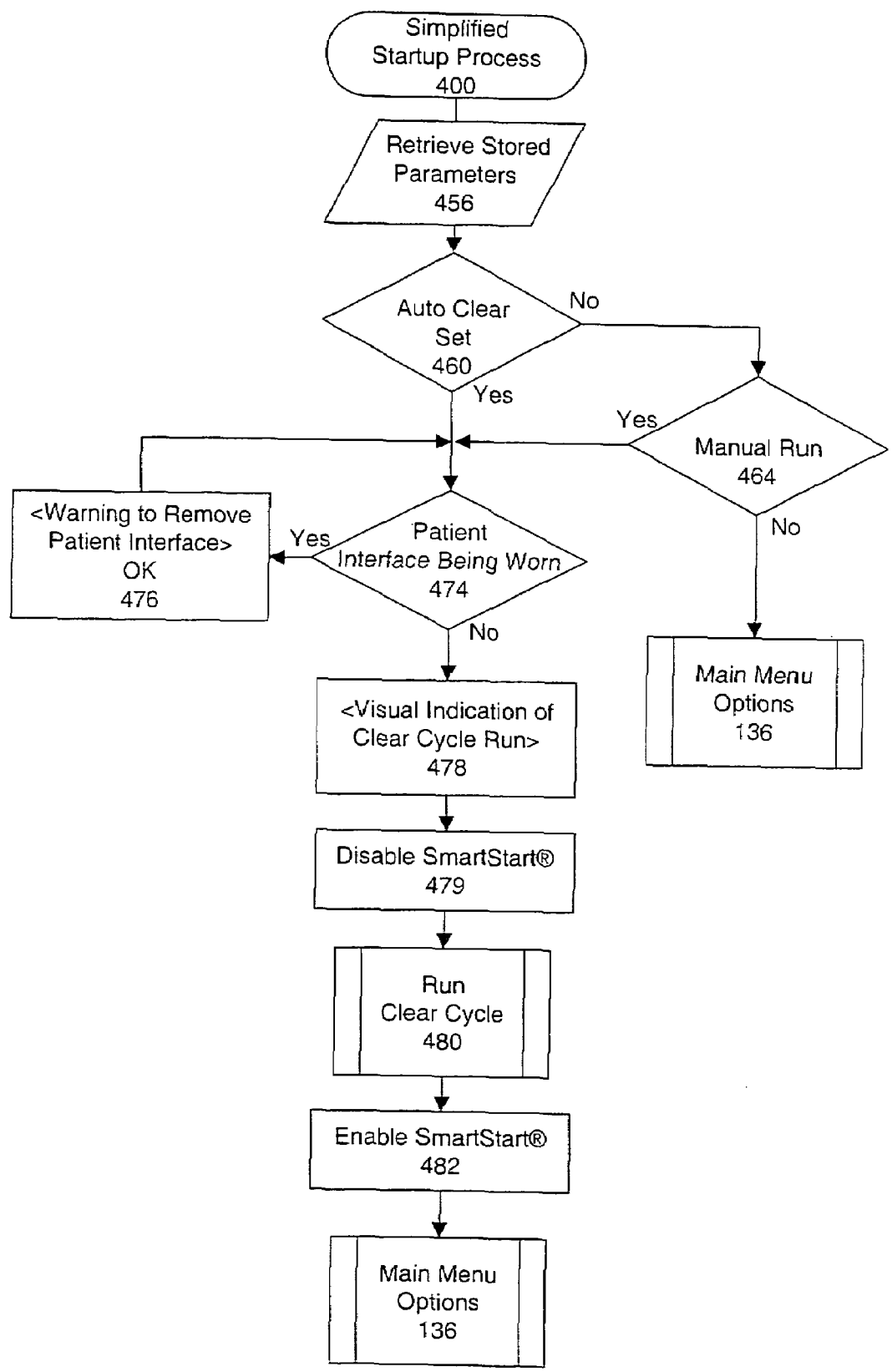
FIG. 6 is a flow chart of a simplified startup process.
Figure 7:
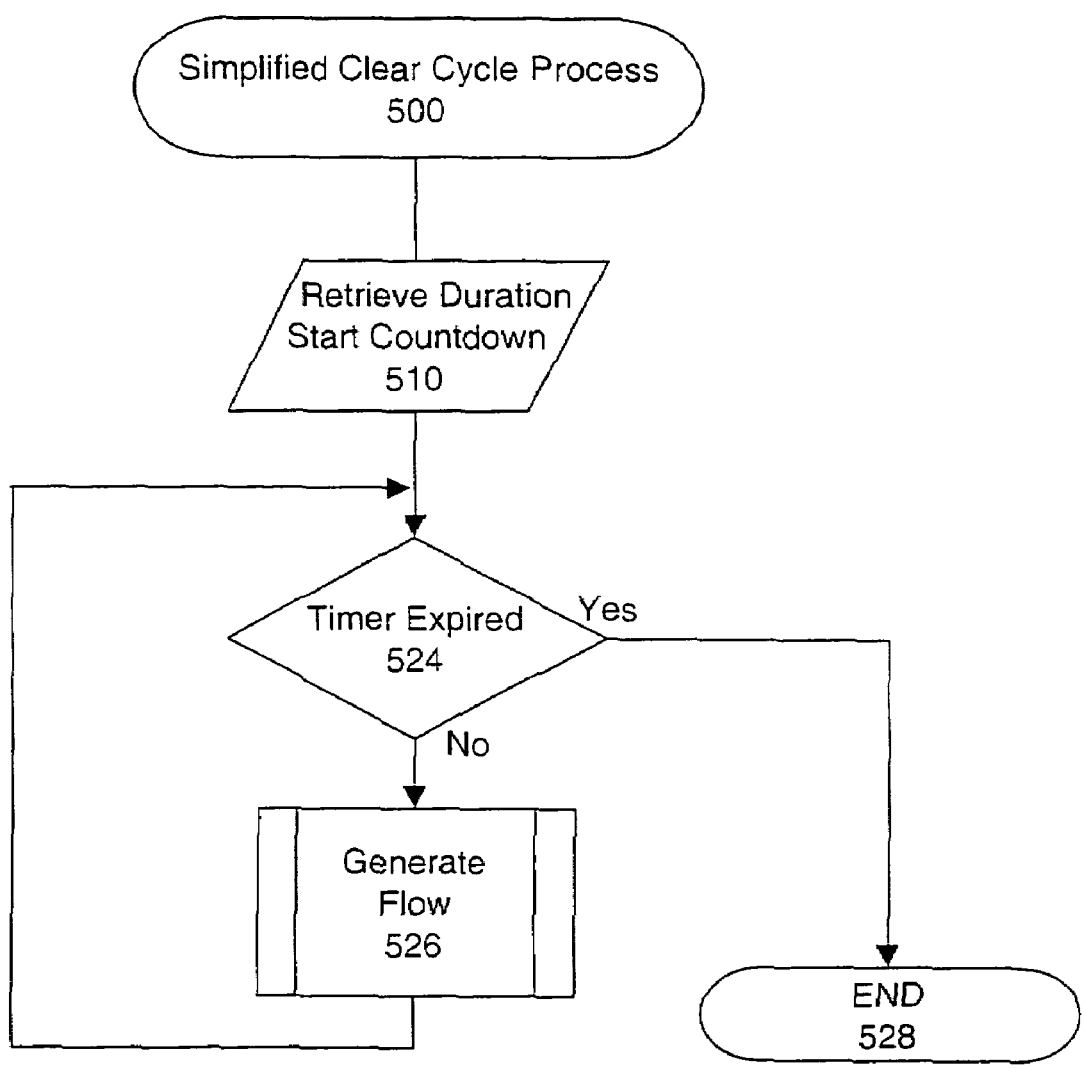
FIG. 7 is a flow chart of a simplified clear cycle process.

FIGS. 5-7 illustrate flow charts of a simplified embodiment of a clear cycle. In this embodiment, various features in the embodiment illustrated in FIGS. 2-4 are omitted. For example, in a simplified setup process 300, options to choose at what interval to run a clear cycle (steps 114-120 of the setup process 100), whether to disable a reminder (steps 124-128), or whether to set an audible warning (steps 132-134), are omitted. In a simplified startup process 400, checks of the date and/or time to determine if a clear cycle should be run or whether a reminder is set (steps 160-163 of startup process 150) are omitted. Some of the audio and visual warnings (steps 166-170) are omitted as well. In a simplified clear cycle process 500, fault detection steps (steps 212-216 of the clear cycle process 200) are omitted. Additionally, a check for the patient interface 16 being worn is omitted (for example, steps 220 and 222 of the clear cycle process 200). In the simplified embodiments, flow is delivered below 15-20 cm $H_2O$ to minimize the chance of damage to the patient's airways if the patient interface 16 is inadvertently worn during clear cycle flow generation. Of course, steps/features from setup process 100, startup process 150, and clear cycle process 200 can be incorporated into the simplified embodiments.

FIG. 5 illustrates the simplified setup process 300. The simplified setup process 300 queries at step 310 whether to perform the simplified setup process 300 to obtain information from the patient. The patient can select "No" and exit to main menu options 136. If the patient selects "Yes," the simplified setup process 300 proceeds from step 310 to step 312, at which step the simplified setup process 300 queries for the duration of the clear cycle (typically in the form of a time in seconds). After obtaining the clear cycle duration at step 312, the simplified setup process 300 proceeds to step 322. At step 322, the simplified setup process 300 queries whether to run a clear cycle automatically upon startup of the ventilation device 10. If the patient selects "Yes" at step 322, the simplified setup process 300 proceeds to step 330 at which step a corresponding operational parameter 36 is stored and the patient acknowledges that auto clear is set by selecting "OK." The simplified setup process 300 then proceeds to the main menu options at step 136. If, at step 322, the patient selects "No" to running an auto clear on startup, the simplified setup process 300 proceeds to the main menu options 136 without setting an operational parameter 36 corresponding to performing an auto clear. The simplified setup process 300 can include a check for disabling a reminder, as shown, for example, in steps 124-128 of the setup process 100 illustrated in FIG. 2B.

FIG. 6 illustrates a simplified startup process 400. At step 456, the simplified startup process 400 retrieves the stored operational parameters 36 corresponding to whether to run the clear cycle automatically and the duration of the clear cycle (parameters typically obtained during operation of the simplified setup process 300). At step 460, the simplified startup process 400 checks whether the auto clear parameter is set. If not, the simplified startup process 400 proceeds to step 464 and the patient can select whether to manually run a clear cycle. If the patient does not select to manually run a clear cycle, the simplified startup process 400 exits to the main menu options at step 136. If the auto clear is set (step 460), or if the patient selects to perform a manual run (step 464), the simplified startup process 400 proceeds to step 474. It is contemplated that, for example, a check to perform a manual clear cycle at step 464 can be omitted.

The simplified startup process 400 determines at step 474 whether the patient interface 16 is being worn, and warns the patient at step 476 to remove the patient interface and acknowledge that it is "OK" to proceed. After determining that the patient interface is not being worn at steps 474 and 476, the simplified startup process 400 proceeds to step 478 and the controller 18 instructs the display 34 to display a visual indication of the clear cycle. SmartStart is disabled at step 479, the simplified clear cycle is run at step 480, and SmartStart is enabled at step 482. The simplified startup process 400 ends by returning to main menu options at step 136.

The simplified clear cycle process 500 (called by step 480 of the simplified startup process 400) is illustrated in FIG. 7. Upon running the simplified clear cycle process 500, a stored operational parameter 36 is retrieved at step 510, corresponding to the duration that flow should be generated. Additionally, a timer countdown is started, counting down a period of time corresponding to the retrieved duration. The simplified clear cycle process 500 then proceeds to step 524, at which point the controller 18 determines whether the count down timer has expired. If the countdown has not expired, the simplified clear cycle process 500 proceeds to generate flow at step 526. Flow is typically generated at a pressure below 15-20 cm $H_2O$. Accordingly, if the patient interface 16 is inadvertently worn, damage to the patient's airways caused by excessive flow pressure can be avoided. Of course, a preliminary check to make sure the patient interface 16 is not worn has already been performed (for example at steps 474 and 476 of the simplified startup process 400). The simplified clear cycle process 500 proceeds to step 524 to again check whether the timer has expired. If it is determined that the timer has expired at step 524, flow is no longer generated and the simplified clear cycle process 500 ends at step 528 (and returns to step 482 of the simplified startup process 400).

Although the clear cycle has been described in conjunction with a ventilation device which does not include a humidifier, the clear cycle can also be implemented in a ventilation device with a humidifier. The humidifier may be provided with one or more pressure/flow sensors having output incorporated into the clear cycle program.

Further, it is contemplated that the clear cycle program may include not only the existence of a blockage, but also the location of the blockage, e.g., by identifying the position of sensors which indicate an unusual or unexpected level of pressure and/or flow. The display could provide an indication of the position of the sensors between which a problem may be found. Alternatively, or in addition, the sensors may be provided with a light and/or sound producing device to indicate the position of the obstruction.

Further, the clear cycle may be manually activated. The manual activation mode can be used in addition to, or instead of, the periodic activation which is automatically carried out by the controller, as described in relation to FIG. 2A. For example, the user or operator could press one or more buttons to start and implement the clear cycle for as long as the buttons are held down. Preferably, a specific button or selection of buttons would be preferable to avoid inadvertent activation. In one form, the clinical menu can be accessed, and one prompt on the LCD may be "For Clear Cycle Press 'UP' for 3 seconds then 'START'". Of course, other ways to manually activate the clear cycle are contemplated which are within the scope of the present invention.

The foregoing specific embodiments have been provided to illustrate principles of the present invention and are not intended to be limiting. To the contrary, the present invention is intended to encompass all modification, alterations, and substitutions within the spirit and scope consistent with the principles and novel features disclosed in any fashion herein.

What is claimed is:

1. A method of performing a clear cycle in a ventilatory assistance apparatus including a flow generator in fluid communication with a patient interface in a flow path, the method comprising:
   examining a plurality of operational parameters;
   determining whether the flow generator should generate flow based on at least one of the plurality of operational parameters;
   warning the patient to avoid interfacing with the patient interface of the ventilation device prior to generating the flow; and
   operating the flow generator to generate the flow in accordance with at least one of the plurality of operational parameters.

2. The method of claim 1, further comprising monitoring a plurality of sensors indicative of flow conditions in the flow path.

3. The method of claim 2, further comprising obtaining at least one of the plurality of operational parameters via the plurality of sensors.

4. The method of claim 1, further comprising monitoring a plurality of sensors indicative of whether the patient interface is being worn by the patient.

5. The method of claim 4, further comprising obtaining at least one of the plurality of operational parameters via the plurality of sensors.

6. The method of claim 1, further comprising obtaining at least one of the plurality of operational parameters prior to performing the clear cycle.

7. The method of claim 1, further comprising obtaining at least one of the plurality of operational parameters via a menu interface.

8. The method of claim 1, further comprising obtaining at least one of the plurality of operational parameters during a setup process.

9. The method of claim 1, further comprising storing at least one of the plurality of operational parameters in a recordable medium.

10. The method of claim 1, further comprising storing at least one of the plurality of operational parameters at a remote location.

11. The method of claim 1, further comprising transmitting at least one of the plurality of operational parameters via a public communication system.

12. The method of claim 1, further comprising obtaining at least one of the plurality of operational parameters from a pre-recorded medium.

13. The method of claim 1, further comprising obtaining at least one of the plurality of operational parameters from a remote location.

14. The method of claim 1, further comprising receiving at least one of the plurality of operational parameters via a public communication system.

15. The method of claim 1, further comprising performing the clear cycle automatically based upon at least one of the plurality of operational parameters.

16. The method of claim 15, further comprising performing the clear cycle automatically at an interval based upon at least one of the plurality of operational parameters.

17. The method of claim 16, further comprising determining the duration of the interval based upon an internal real-time clock.

18. The method of claim 16, further comprising determining the duration of the interval based upon an internal timer.

19. The method of claim 16, further comprising determining the duration of the interval based upon an external signal.

20. The method of claim 1, further comprising providing a reminder to perform the clear cycle based upon at least one of the plurality of operational parameters.

21. The method of claim 20, further comprising providing the reminder to the patient.

22. The method of claim 20, further comprising providing the reminder to a remote site.

23. The method of claim 20, further comprising providing the reminder at an interval based upon at least one of the plurality of operational parameters.

24. The method of claim 23, further comprising determining the duration of the interval based upon an internal real-time clock.

25. The method of claim 23, further comprising determining the duration of the interval based upon an internal timer.

26. The method of claim 23, further comprising determining the duration of the interval based upon an external signal.

27. The method of claim 1, further comprising operating the flow generator to deliver flow at a pressure and rate which are based upon at least one of the plurality of operational parameters.

28. The method of claim 1, further comprising operating the flow generator to deliver flow at a predetermined pressure and rate.

29. The method of claim 28, wherein the predetermined pressure and rate correspond to a maximum pressure at the patient interface of 15-20 cm $H_2O$ in the case that the patient interface is worn during the clear cycle.

30. The method of claim 1, further comprising operating the flow generator to deliver flow at maximum pressure and rate based upon at least one of the plurality of operational parameters including an indication that the patient interface is not being worn by the patient during the clear cycle.

31. The method of claim 30, further comprising halting operation of the flow generator to prevent flow at maximum pressure and rate based upon at least one of the plurality of operational parameters including an indication that the patient interface is being worn by the patient during the clear cycle.

32. The method of claim 31, wherein the indication whether the patient interface is being worn by the patient during the clear cycle is based upon heat or pressure sensing.

33. The method of claim 1, further comprising performing the clear cycle for a duration based on at least one of the plurality of operational parameters.

34. The method of claim 33, wherein the duration for operating the flow generator is based on a countdown timer.

35. The method of claim 1, further comprising communicating status of the clear cycle via a visual interface.

36. The method of claim 35, wherein the visual interface comprises an LCD display readout.

37. The method of claim 1, further comprising communicating status of the clear cycle via an audio interface.

38. The method of claim 37, wherein the audio interface comprises a buzzer configured to produce an alarm.

39. The method of claim 37, wherein the audio interface comprises a speaker configured to produce an informative voice prompt.

40. The method of claim 1, wherein the operational parameters include an indication of a duration of the clear cycle, an interval corresponding to how often the clear cycle should be run, an indication of whether to run the clear cycle automatically upon startup, an indication of whether to disable a clear cycle reminder, and an indication of whether to provide an audible warning.

41. The method of claim 1, further comprising monitoring the operational parameters to determine whether a fault condition has occurred.

42. The method of claim 41, further comprising determining whether the fault condition is caused by blocking debris in the flow path.

43. The method of claim 41, wherein the fault condition is indicated by a visual warning.

44. The method of claim 41, wherein the fault condition is indicated by an audible warning.

45. The method of claim 41, further comprising stopping the flow generator upon determining that the fault condition has occurred.

46. The method of claim 41, further comprising generating flow for a predetermined duration at a predetermined pressure upon determining that the fault condition has occurred.

47. The method of claim 41, further comprising setting the ventilatory assistance apparatus into a service required mode upon determining that the fault condition has occurred.

48. The method of claim 41, wherein the determination that the fault condition has occurred is based on at least one of the operational parameters.

49. The method of claim 48, wherein the at least one of the operational parameters is obtained via a plurality of sensors indicative of flow conditions in the flow path.

50. The method of claim 41, further comprising recording a description of the fault condition upon determining that the fault condition has occurred.

51. The method of claim 41, further comprising transmitting to a remote location a description of the fault condition upon determining that the fault condition has occurred.

52. A ventilatory assistance apparatus including a flow generator in fluid communication with a patient interface in a flow path, configured to perform a clear cycle, comprising:

a data storage configured to store a plurality of operational parameters;

a controller configured to determine whether the flow generator should generate flow based on at least one of the plurality of operational parameters; and a display configured to warn the patient to avoid interfacing with the patient interface of the ventilation device prior to the controller determining that the flow generator should generate the flow;

wherein the controller instructs the flow generator to generate the flow in accordance with at least one of the plurality of operational parameters.

53. A computer-readable medium carrying one or more instructions for performing a clear cycle in a ventilatory assistance apparatus including a flow generator in fluid communication with a patient interface in a flow path, the instructions comprising:

examining a plurality of operational parameters;

determining whether a flow should be generated based on at least one of the plurality of operational parameters;

warning the patient to avoid interfacing with the patient interface of the ventilation device prior to generating the flow; and operating the flow generator to generate the flow in accordance with at least one of the plurality of operational parameters.

54. A computer data signal embodied in a carrier wave including one or more instructions for performing a clear cycle in a ventilatory assistance apparatus including a flow generator in fluid communication with a patient interface in a flow path, the instructions comprising:

examining a plurality of operational parameters;

determining whether a flow should be generated based on at least one of the plurality of operational parameters;

warning the patient to avoid interfacing with the patient interface of the ventilation device prior to generating the flow; and operating the flow generator to generate the flow in accordance with at least one of the plurality of operational parameters.

* * * * *